(12) United States Patent
Hassan et al.

(10) Patent No.: US 8,809,025 B2
(45) Date of Patent: Aug. 19, 2014

(54) ALGAE PROCESSING

(75) Inventors: Abbas Hassan, Sugar Land, TX (US); Aziz Hassan, Sugar Land, TX (US); Rayford G. Anthony, College Station, TX (US); Gregory G. Borsinger, Chatham, NJ (US)

(73) Assignee: H R D Corporation, Houston, TX (US)

( * ) Notice: Subject to any disclaimer, the term of this patent is extended or adjusted under 35 U.S.C. 154(b) by 987 days.

(21) Appl. No.: 12/898,875

(22) Filed: Oct. 6, 2010

(65) Prior Publication Data

US 2011/0245552 A1 Oct. 6, 2011

Related U.S. Application Data

(60) Provisional application No. 61/249,455, filed on Oct. 7, 2009.

(51) Int. Cl.

| C12P 7/64 | (2006.01) |
|---|---|
| C12N 1/12 | (2006.01) |
| C07C 51/43 | (2006.01) |
| F01D 1/02 | (2006.01) |
| C12M 1/00 | (2006.01) |
| C12N 1/06 | (2006.01) |
| C12M 1/33 | (2006.01) |

(52) U.S. Cl.
CPC ............... *C12M 21/12* (2013.01); *C12M 21/02* (2013.01); *C12N 1/12* (2013.01); *Y02E 50/17* (2013.01); *C12N 1/066* (2013.01); *C12M 45/02* (2013.01)
USPC ...... 435/134; 435/257.1; 554/174; 415/208.3

(58) Field of Classification Search
CPC ...... C12M 21/12; C12M 27/00; C12M 27/02; A01H 13/00; A01G 33/00; A01G 31/00
USPC .......................................................... 435/420
See application file for complete search history.

(56) References Cited

U.S. PATENT DOCUMENTS

| 3,887,167 | A | 6/1975 | Irwin | |
|---|---|---|---|---|
| 5,538,191 | A | 7/1996 | Holl | |
| 5,877,350 | A | 3/1999 | Langer et al. | |
| 6,241,472 | B1* | 6/2001 | Bosch et al. ............... | 415/208.3 |
| 6,368,366 | B1 | 4/2002 | Langer et al. | |
| 6,368,367 | B1 | 4/2002 | Langer et al. | |
| 6,383,237 | B1 | 5/2002 | Langer et al. | |
| 6,530,964 | B2 | 3/2003 | Langer et al. | |
| 6,742,774 | B2 | 6/2004 | Holl | |
| 6,809,071 | B2* | 10/2004 | Hasegawa et al. ............ | 510/145 |
| 2003/0043690 | A1 | 3/2003 | Holl | |
| 2004/0052158 | A1 | 3/2004 | Holl | |
| 2005/0033069 | A1 | 2/2005 | Holl et al. | |
| 2007/0048848 | A1* | 3/2007 | Sears ............................. | 435/134 |
| 2009/0005605 | A1 | 1/2009 | Hassan et al. | |

FOREIGN PATENT DOCUMENTS

| WO | 9858740 | 12/1998 |
|---|---|---|
| WO | 2002064708 A2 | 8/2002 |
| WO | 2008053174 | 5/2008 |

OTHER PUBLICATIONS

IKA-Rotor-Stator Generators—2003 Processing Ctalog (38 pgs.).
Gogate, et al. "Cavitation: A technology on the horizon," Current Science 91, No. 1, Jul. 2006, pp. 35-46 (12 pgs.).
Office Action dated Jun. 25, 2009 for U.S. Appl. No. 12/142,447 (10 pgs.).
Office Action dated Jan. 7, 2010 for U.S. Appl. No. 12/142,447 (6 pgs.).
Office Action dated May 13, 2010 for U.S. Appl. No. 12/142,447 (5 pgs.).
Office Action dated Feb. 4, 2010 for U.S. Appl. No. 12/492,721 (5 pgs.).
Office Action dated Feb. 18, 2010 for U.S. Appl. No. 12/635,433 (6 pgs.).
Office Action dated Feb. 18, 2010 for U.S. Appl. No. 12/635,454 (6 pgs.).
Office Action dated May 14, 2010 for U.S. Appl. No. 12/137,441 (15 pgs.).
Office Action dated Feb. 19, 2010 for U.S. Appl. No. 12/144,459 (10 pgs.).
Office Action dated Sep. 2, 2009 for U.S. Appl. No. 12/142,433 (11 pgs.).
Office Action dated Jan. 29, 2010 for U.S. Appl. No. 12/142,433 (8 pgs.).
Office Action dated May 24, 2011 for U.S. Appl. No. 12/142,433 (10 pgs.).
Office Action dated Apr. 30, 2010 for U.S. Appl. No. 12/141,191 (12 pgs.).
Office Action dated Oct. 27, 2009 for U.S. Appl. No. 12/142,120 (15 pgs.).
Office Action dated May 5, 2010 for U.S. Appl. No. 12/571,537 (12 pgs.).
Office Action dated Feb. 24, 2011 for U.S. Appl. No. 12/796,358 (13 pgs.).

(Continued)

*Primary Examiner* — Annette Para
(74) *Attorney, Agent, or Firm* — Timothy S. Westby; Porter Hedges, LLP.

(57) ABSTRACT

A method for culturing algae comprising, forming an emulsion comprising a gaseous stream and a media utilizing a high shear device, wherein the emulsion comprises gas bubbles, and wherein the high shear device comprises at least one toothed rotor and at least one stator; introducing the emulsion into a bioreactor; and introducing an algae into the bioreactor for growing the algae culture. Additionally, a method for producing liquids from an algae culture, the method comprising forming an emulsion comprising a buffer and algal components, wherein the emulsion comprises algal component globules; separating algal hydrocarbons; and processing algal hydrocarbons to form liquid hydrocarbons. Additionally, a system for producing liquids from an algae culture comprising at least one high shear device.

19 Claims, 3 Drawing Sheets

(56) References Cited

OTHER PUBLICATIONS

Office Action dated Feb. 29, 2012 for U.S. Appl. No. 12/146,733 (8 pgs.).
Office Action dated Jun. 3, 2011 for U.S. Appl. No. 12/568,155 (11 pgs.).
Office Action dated Jun. 2, 2011 for U.S. Appl. No. 12/427,286 (12 pgs.).
Office Action dated Jun. 3, 2011 for U.S. Appl. No. 12/568,280 (16 pgs.).
IKA, "Introduction to IKA's Three Stage Dispax Reactor," Retrieved from <http://www.ikausa.com/pdfs/process/dr%202000-Homogenizing-Dispersing-Suspending-Emulsifying.pdf> on Aug. 22, 2012 (12 pgs.).
IKA-DRS Reactors website http://www.ikausa.com/dr.him, on Sep. 8, 2010 (2 pgs.).
International Preliminary Report on Patentability dated Apr. 19, 2012 for corresponding International Application No. PCT/US2010/051569 (7 pgs.).
Chinese Office Action dated Jan. 22, 2013 for corresponding Chinese Application No. 201080045469.7 (12 pgs.).
Chinese Office Action dated Sep. 29, 2013 for corresponding Chinese Application No. 201080045469.7 (14 pgs.).
European Search Report dated May 21, 2013 for corresponding European Application No. 10822576.4 (6 pgs.).
Zhang et al., "Microbubble Fermentation of Recombinant Pichia pastoris for Human Serum Albumin Production", Process Biochemistry, Elsevier, vol. 40, No. 6, dated May 1, 2005, pp. 2073-2078 (6 pgs.).
Miron et al., "Bubble-Column and Airlift Photobioreactors for Algal Culture", AIChE Journal, vol. 46, No. 9, dated Sep. 1, 2000, pp. 1872-1887 (16 pgs.).
Hensirisak et al., "Scale-Up of Microbubble Dispersion Generator for Aerobic Fermentation", Applied Biochemistry and Biotechnology-Part A Enzyme Engineering and Biotechnology 2002 US, vol. 101, No. 3, dated 2002, pp. 211-227 (17 pgs.).
Zimmerman et al., "Towards Energy Efficient Nanobubble Generation with Fluidic Oscillation", Current Opinion in Colloid and Interface Science, London, GB, vol. 16, No. 4, dated Jan. 31, 2011, pp. 350-356 (7 pgs.).
Ying et al., "Growth Enhancement of Dunaliella saline by Microbubble Induced Airlift Loop Bioreactor (ALB)-The Relation Between Mass Transfer and Growth Rate", Journal of Biomaterials and Nanobiotechnology, vol. 4, dated Apr. 1, 2013, pp. 1-9 (9 pgs.).

\* cited by examiner

ALGAE PROCESSING

CROSS-REFERENCE TO RELATED APPLICATIONS

This application claims the benefit under 35 U.S.C. §119(e) of U.S. Provisional Patent Application No. 61/249,455 filed Oct. 7, 2009, the disclosure of which is hereby incorporated herein by reference.

STATEMENT REGARDING FEDERALLY SPONSORED RESEARCH OR DEVELOPMENT

Not Applicable.

BACKGROUND OF THE INVENTION

1. Technical Field

The present disclosure relates generally to the production of biofuels. More specifically, the disclosure relates to a high shear process for culturing algae.

2. Background of the Invention

Petroleum reserve depletion, economic, and environmental pressures have influenced and reduced the production and refining of petroleum derived liquid fuels. As a result, increasing interest and investment into renewable sources of liquid hydrocarbons has accelerated. However, dependency on crop-derived biofuels is limited by growing season, harvesting, and limited crop viability. Further, the reliance on food-crops for biofuels represents a supply-side strain on worldwide foodstuffs, from grains to livestock, food-crop implementation faces increased hurdles to economic, long-term, viability as a source for liquid fuel replacement.

Algae do not face the same hurdles to viability for bio fuels applications as crops, as they may be cultured and harvested year-round on relatively small land areas. Further, many algae have been discovered to produce significant quantities of upgradeable hydrocarbons, such as lipids. However, as water-living, carbon-fixing organisms, the development and storage of these hydrocarbons is limited by the diffusion of carbonaceous gases, such as carbon dioxide, through water. Alternate growth media, gas bubblers, and fluid beds implemented currently have not resulted in increased hydrocarbon production, as the diffusion of gases through the algae media limits carbon available for fixation, growth, and storage.

During harvesting, the quantity of hydrocarbons available for refining does not reach the theoretical yield calculated for a given algae density. As the harvesting, lysing, and separation steps in conventional processes are slow, on the scale of seconds and minutes, the hydrocarbon/lipids exposed to free radicals, digestive enzymes, and other intracellular biological compounds rapidly degrade. Biological degradation represents an additional hurdle to efficient conversion of algal biomass to upgradeable hydrocarbons. As such, industrial scale algal biofuels represent an equally inefficient resource.

SUMMARY

A method for alga-culture, the method comprising, forming an emulsion comprising a gaseous stream and a media utilizing a high shear device, wherein the emulsion comprises gas bubbles with a mean diameter of less than about 5 μm, and wherein the high shear device comprises at least one rotor and at least one stator; introducing the emulsion into a bioreactor; and introducing an algae into the bioreactor for culturing the algae culture.

A method for culturing algae for producing liquid hydrocarbons, the method comprising, forming a first emulsion comprising a gaseous stream and a media utilizing a high shear device, wherein the first emulsion comprises gas bubbles with a mean diameter of less than about 5 μm, and wherein the high shear device comprises at least one rotor and at least one stator; introducing the first emulsion into a bioreactor; introducing at least one algae into the first emulsion in the bioreactor, for producing an algae culture; forming a second emulsion comprising a portion of the algae culture and a buffer utilizing a high shear device, wherein the second emulsion comprises lysed algal-component globules with a mean diameter of less than about 5 μm, and wherein the lysed algal component globules comprise algal hydrocarbons and algal biomolecules; separating algal hydrocarbons from algal biomolecules in the second emulsion; and processing the algal hydrocarbons to produce liquid hydrocarbons.

A system for culturing algae in liquid hydrocarbon production comprising: a liquid media stream; a gaseous stream; a buffer stream; a bioreactor configured for aquaculture; a separator; and at least one high shear device having at least one toothed rotor and at least one stator, wherein the at least one high shear device is in fluid communication with the liquid media stream, the gaseous stream, the buffer stream, the bioreactor, and the separator.

These and other embodiments, features, and advantages will be apparent in the following detailed description and drawings.

BRIEF DESCRIPTION OF THE DRAWINGS

For a more detailed description of the preferred embodiment of the present invention, reference will now be made to the accompanying drawings, wherein.

DETAILED DESCRIPTION

Figure 1:
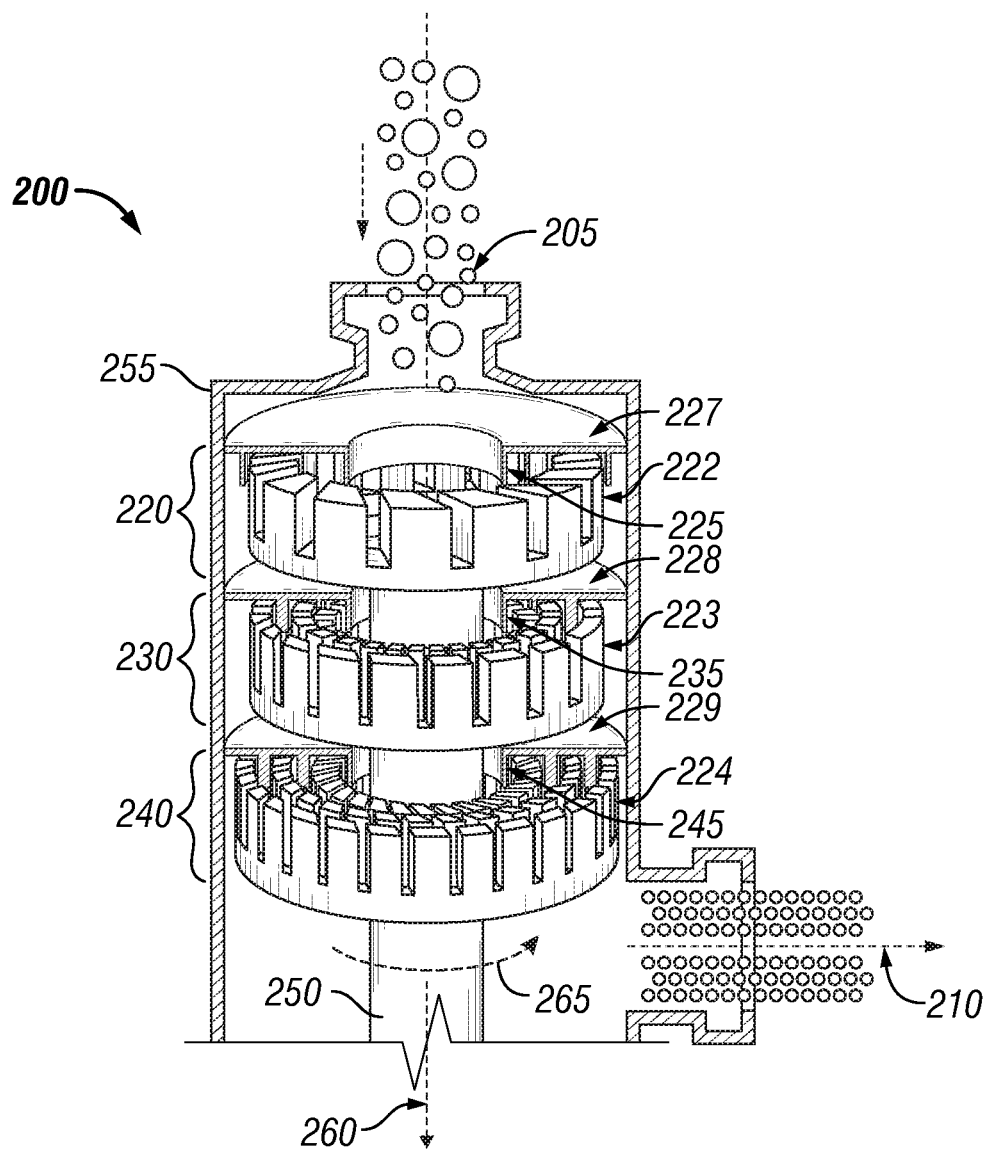
FIG. 1 is a cross-sectional diagram of a high shear device for the processing of algae.

Overview: The present disclosure provides a system and method for algae production, harvesting, and processing with at least one high shear device. Algae are diverse group of photosynthetic organisms that typically grow in bodies of water as unicellular or multicellular forms. As aquatic or marine organisms, algae acquire the carbon dioxide necessary for photosynthesis by Brownian motion and diffusion. Further, certain species of algae fix carbon derived from carbon dioxide to produce and store fatty oils, carbohydrates, proteins, polysaccharides, and other compounds, hereinafter hydrocarbons. The acquisition of carbon dioxide, hereinafter $CO_2$, from water represents a limiting step in growth rate and storage of these compounds. As certain algae are potentially useable in liquid fuel production, the uptake and fixation of carbon is a limiting step in preparing alga-derived biofuels.

Further, after growth in the culture the algae are harvested, lysed, and the desired hydrocarbons are separated from other biological molecules. The process of lysing the algae exposes the hydrocarbons to intracellular compounds, enzymes, and free radicals that degrade the hydrocarbon chains. These intracellular compounds reduce the hydrocarbon yields. Conventionally, buffers and chelators for these intracellular compounds are limited in their protection of the hydrocarbons by the rates of diffusion and Brownian motion. The limits of buffers for chelating these compounds represent a product limitation for the harvesting algae and isolation of hydrocarbons for processing into liquid fuels.

A system and method employ a high shear mechanical device to provide rapid contact and mixing of chemical ingredients in a controlled environment in the reactor/mixer device. The high shear device reduces the mass transfer limitations on the reaction and thus increases the overall reaction rate. Chemical reactions and mixtures involving liquids, gases, and solids rely on the laws of kinetics that involve time, temperature, and pressure to define the rate of reactions. Where it is desirable to react two or more raw materials of different phases (e.g. solid and liquid; liquid and gas; solid, liquid and gas), one of the limiting factors controlling the rate of reaction is the contact time of the reactants. In the case of heterogeneously catalyzed reactions, there may be an additional rate limiting factor, namely, removing the reaction products from the surface of the catalyst to enable the catalyst to catalyze further reactants.

In conventional processes, contact time for the reactants and/or catalyst may be altered by mixing which provides contact between two or more reactants involved in a chemical reaction. A reactor assembly that comprises a high shear device makes possible decreased mass transfer limitations and thereby allows the reaction to more closely approach kinetic limitations. When reaction rates are accelerated, residence times may be decreased, thereby increasing obtainable throughput and production. Alternatively, where the current yield is acceptable, decreasing the required residence time allows for the use of smaller amounts of reactant, thus improving the process economics.

High Shear Device: High shear devices (HSD) such as high shear mixers and high shear mills, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid. The classes are distinguished based on delivered energy density. There are three classes of industrial mixers having sufficient energy density to consistently produce mixtures or emulsions with particle or bubble sizes in the range of 0 to 50 μm.

Homogenization valve systems are typically classified as high-energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and may yield average particle size range from about 0.01 μm to about 1 μm. At the other end of the spectrum are high shear mixer systems classified as low energy devices. These systems usually have paddles or fluid rotors that turn at high speed in a reservoir of fluid to be processed, which in many of the more common applications is a food product. These systems are usually used when average particle, globule, or bubble, sizes of greater than 20 microns are acceptable in the processed fluid.

Between low energy—high shear mixers and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which may be in the range of from about 0.025 mm to 10.0 mm. Rotors may preferably be driven by an electric motor through a direct drive or belt mechanism. Many colloid mills, with proper adjustment, may achieve average particle, or bubble, sizes of about 0.01 μm to about 25 μm in the processed fluid. These capabilities render colloid mills appropriate for a variety of applications including colloid and oil/water-based emulsion processing such as preparation of cosmetics, mayonnaise, silicone/silver amalgam, and roofing-tar mixtures.

Referring now to FIG. 1, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 are configured to rotate about axis 260, in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances, the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. In further designs, the rotors 222, 223, and 224 may comprise multiple concentric rows of rotor teeth. Stators 227, 228, and 229 may comprise a number of stator teeth circumferentially spaced about the circumference of each stator. In further designs, the stators 227, 228, and 229 may comprise multiple concentric rows of stator teeth.

In embodiments, the inner diameter of the rotor is about 11.8 cm. In embodiments, the outer diameter of the stator is about 15.4 cm. In further embodiments, the rotor and stator may have an outer diameter of about 60 mm for the rotor, and about 64 mm for the stator. Alternatively, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets, or globules, of a fluid that is insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired bubble size, if feedstream 205 comprises a gas, or globule size, if feedstream 205 comprises a liquid, in the product dispersion 210.

The product dispersion 210 of gas particles, globules, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, globule or bubble, size less than about 1.5 μm; preferably the globules are sub-micron in diameter. In certain instances, the average globule size is in the range from about 1.0 μm to about 0.1 μm. Alternatively, the average globule size is less than about 400 nm (0.4 μm) and most preferably less than about 100 nm (0.1 μm).

Tip speed is the velocity (m/sec) associated with the end of one or more revolving elements that is transmitting energy to the reactants. Tip speed, for a rotating element, is the circumferential distance traveled by the tip of the rotor per unit of time, and is generally defined by the equation $V$ (m/sec) $=\pi \cdot D \cdot n$, where V is the tip speed, D is the diameter of the rotor, in meters, and n is the rotational speed of the rotor, in revolutions per second. Tip speed is thus a function of the rotor diameter and the rotation rate.

For colloid mills, typical tip speeds are in excess of 23 m/sec (4500 ft/min) and may exceed 40 m/sec (7900 ft/min). For the purpose of the present disclosure the term 'high shear' refers to mechanical rotor-stator devices, such as mills or mixers, that are capable of tip speeds in excess of 5 m/sec (1000 ft/min) and require an external mechanically driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip of the shear mixer are produced during operation. In certain embodiments, the local pressure is at least about 1034 MPa (about 150,000 psi). The local pressure further depends on the tip speed, fluid viscosity, and the rotor-stator gap during operation.

An approximation of energy input into the fluid (kW/l/min) may be made by measuring the motor energy (kW) and fluid output (l/min). In embodiments, the energy expenditure of a high shear device is greater than 1000 W/m$^3$. In embodiments, the energy expenditure is in the range of from about 3000 W/m$^3$ to about 7500 W/m$^3$. The high shear device 200 combines high tip speeds with a very small shear gap to produce significant shear on the material. The amount of shear is typically dependent on the viscosity of the fluid. The shear rate generated in a high shear device 200 may be greater than 20,000 s$^{-1}$. In embodiments, the shear rate generated is in the range of from 20,000 s$^{-1}$ to 100,000 s$^{-1}$.

The high shear device 200 produces a gas emulsion capable of remaining dispersed at atmospheric pressure for at least about 15 minutes. For the purpose of this disclosure, an emulsion of gas particles, globules or bubbles, in the dispersed phase in product dispersion 210 that are less than 1.5 μm in diameter may comprise a micro-foam. Not to be limited by a specific theory, it is known in emulsion chemistry that sub-micron particles, globules, or bubbles, dispersed in a liquid undergo movement primarily through Brownian motion effects. The globules in the emulsion of product dispersion 210 created by the high shear device 200 may have greater mobility through boundary layers of solid catalyst particles, thereby facilitating and accelerating the catalytic reaction through enhanced transport of reactants.

The rotor is set to rotate at a speed commensurate with the diameter of the rotor and the desired tip speed as described hereinabove. Transport resistance is reduced by incorporation of high shear device 200 such that the velocity of the reaction is increased by at least about 5%. Alternatively, the high shear device 200 comprises a high shear colloid mill that serves as an accelerated rate reactor. The accelerated rate reactor comprises a single stage, dispersing chamber. The accelerated rate reactor comprises a multiple stage inline disperser comprising at least 2 stages.

Selection of the high shear device 200 is dependent on throughput requirements and desired particle or bubble size in the outlet dispersion 210. In certain instances, high shear device 200 comprises a DISPAX REACTOR® of IKA® Works, Inc. Wilmington, NC and APV North America, Inc. Wilmington, MA. Model DR 2000/4, for example, comprises a belt drive, 4M generator, PTFE sealing ring, inlet flange 1" sanitary clamp, outlet flange ¾" sanitary clamp, 2HP power, output speed of 7900 rpm, flow capacity (water) approximately 300 l/h to approximately 700 l/h (depending on generator), a tip speed of from 9.4 m/s to about 41 m/s (about 1850 ft/min to about 8070 ft/min) Several alternative models are available having various inlet/outlet connections, horsepower, tip speeds, output rpm, and flow rate.

Without limitation by theory a toothed rotor and stator combination provides increased reactant exposure to multiple shear gaps when compared to other shear devices described herein. Additionally, the reactants are subjected to increasing shear as the reactants move radially outward between each rotor and stator combination. The difference in rotational rate accounts for an increasing shear as the reactants are exposed to teeth or rows of teeth found in each rotor/stator combination.

Without wishing to be limited to a particular theory, it is believed that the level or degree of high shear mixing is sufficient to increase rates of mass transfer and may produce localized non-ideal conditions that enable reactions to occur that would not otherwise be expected to occur based on Gibbs free energy predictions. Localized non-ideal conditions are believed to occur within the high shear device resulting in increased temperatures and pressures with the most significant increase believed to be in localized pressures. The increase in pressures and temperatures within the high shear device are instantaneous and localized and quickly revert to bulk or average system conditions once exiting the high shear device. In some cases, the high shear-mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid microcirculation (acoustic streaming). An overview of the application of cavitation phenomenon in chemical/physical processing applications is provided by Gogate et al., "Cavitation: A technology on the horizon," *Current Science* 91 (No. 1): 35-46 (2006). The high shear-mixing device of certain embodiments of the present system and methods is operated under what are believed to be cavitation conditions effective to dissociate the carbon dioxide into a nanofoam for the optimization of algal growth. In certain instances, the conditions are effective for mechanically disintegrating the algae for extracting hydrocarbons. Further, the conditions may be effective for mechanically homogenizing the hydrocarbon chains to produce liquid hydrocarbon products.

Figure 2:
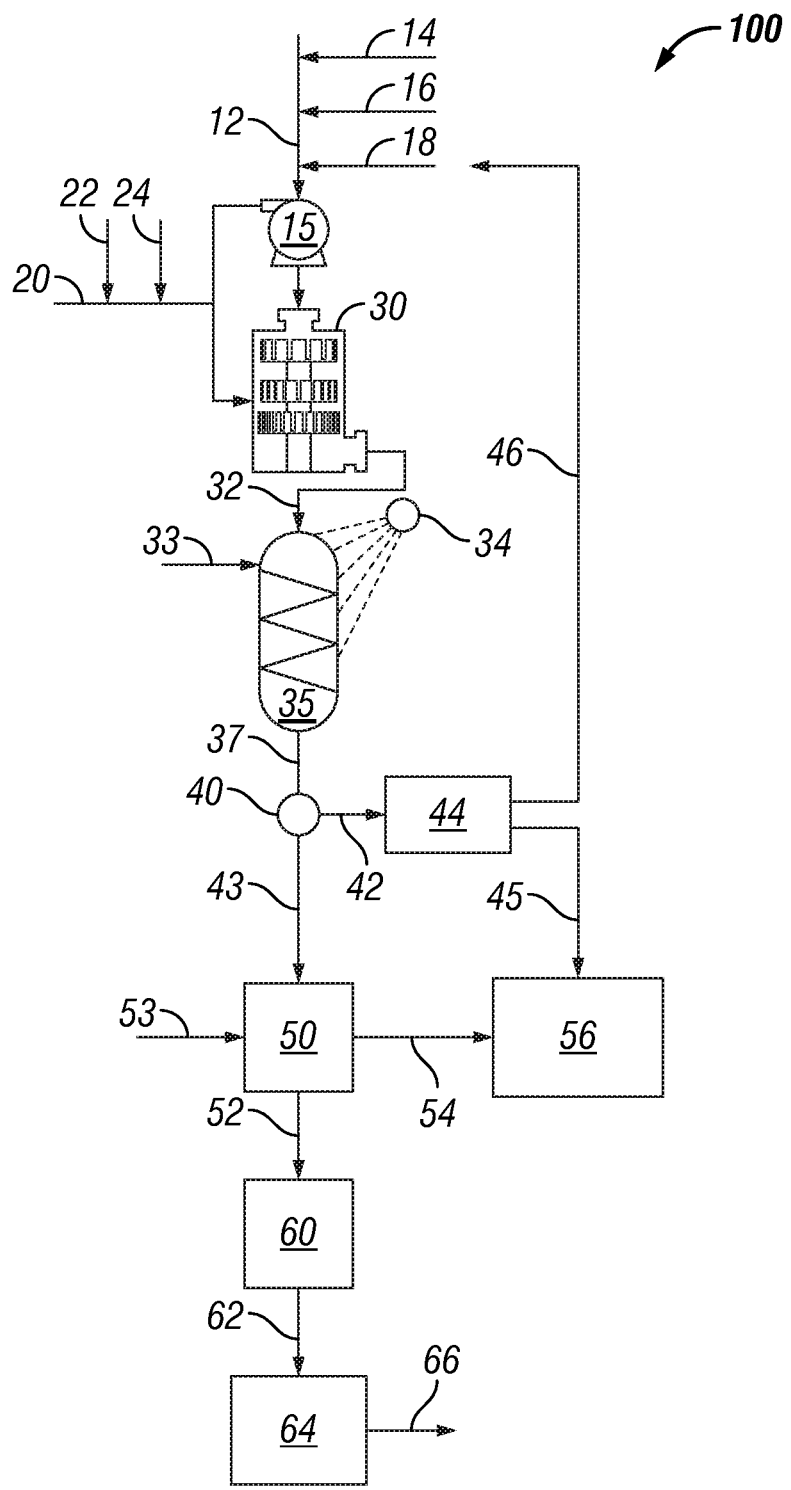
FIG. 2 is a process flow diagram according to an embodiment of the present disclosure for high shear algae processing.

Process and System for Algae Growth and Processing: Referring to FIG. 2, that illustrates an algae processing system (APS) 100. APS 100 comprises high shear device (HSD) 30, bioreactor 35, lysis reactor 50 and hydrocarbon reactor 60. The APS 100 is configured to optimize the growth and harvesting of algae. The APS 100 is configured for introducing a media stream, comprising nutrients, and gases to HSD 30 prior to inoculation with a selected algal species and introduction to a bioreactor 35. Further APS 100 is configured to isolate lipids, oils, and polysaccharides, herein hydrocarbons, from algae. APS 100 is configurable to comprise a plurality of HSD 30 or similar devices. In certain applications, the APS 100 may be configured for the homogenization of the hydrocarbons.

Algae are grown or cultured in a broth or substrate, such as media stream 12. In certain instances, the media stream 12 comprises sugars, proteins, amino acids, and other biomacromolecules suitable to replicate and/or simulate the growth environment of the algae. The presence of these biomolecules in media stream 12 comprises additional molecules for the algal life cycle. Further, the media stream 12 comprises salinity similar to the natural environment of the algae. For instance, the media stream 12 comprises a salinity to replicate an aquatic, a marine, or a brackish environment. Generally, water; preferably distilled water, is used to culture the algae. The water is sterile and free from all contaminants. Any appropriate culture mediums known to those of skill in the art may be used as media stream 12 depending on the specific algae species selected for culturing in APS 100.

In certain instances, media stream 12 is supplemented to improve growth of algae. Media stream 12 comprises a pH enhancer stream 14, an electrolyte stream 16, and a nutrient stream 18. In instances, pH enhancer stream 14, electrolyte stream 16, and nutrient stream 18 comprise media stream 12. Alternatively, pH enhancer stream 14, electrolyte stream 16, and nutrient stream 18 are mixed with media stream 12 to alter, regulate the composition of media stream 12. Further, pH enhancer stream 14, electrolyte stream 16, and nutrient stream 18 are introduced to media stream 12 as a make up stream for replacing the media and nutrients consumed by the algal culture.

A pH enhancer stream 14 is mixed with media stream 12. A pH enhancer stream 14 comprises any chemical understood by one skilled in the art to alter pH. Alternatively, a pH enhancer stream comprises any chemical understood by one skilled in the art to resist pH changes, for instance a buffer. The pH enhancer stream 14 comprises a salt, a buffer, an anion, or a cation without limitation. In instances, pH enhancer stream 14 is introduced directly to media stream 12; alternatively, pH enhancer stream 14 is introduced to APS 100 in any point in the process.

Media stream 12 is supplemented by an electrolyte stream 16. Without limitation by theory, an electrolyte comprises any chemical having free ions. Alternatively, an electrolyte comprises an electrically conductive medium, such as an ionic solution. In certain instances, electrolyte stream 16 comprises magnesium, calcium, sodium, potassium, chloride, phosphate, or carbonate ions, without limitation. Electrolyte stream 16 comprises compounds conducive for the synthesis of chlorophyll; alternatively, for the synthesis of algal hydrocarbons.

Media stream 12 is supplemented with a nutrient stream 18. In certain instances, nutrient stream 18 introduces nutrients, such as but not limited to sugars, lipids, and biomacromolecules. Alternatively, nutrient stream 18 comprises a make-up stream, configured to reintroduce nutrients to media stream 12. Nutrient stream 18 may further comprise antibiotics or antifungal compounds for controlling contaminants in media stream 12.

Media stream 12 is directed to pump 15. Pump 15 is used to provide a controlled flow to HSD 30 and APS 100. Pump 15 increases the pressure of the media stream 12 to greater than about 203 kPa (2 atm). Alternatively, pump 15 may pressurize media stream 12 to a pressure of greater than about 2030 kPa (20 atm). The increased pressure of media stream 12 can be used to accelerate reactions and diffusion of molecules. In further instances, the increased pressure of media stream 12 ensures sterility of the media stream. Without limitation by theory, sterilizing media stream 12 eliminates competitors for nutrients in media stream 12. The limiting factor for pressure in APS 100 may be the pressure limitations of pump 15 and HSD 30. Preferably, all contact parts of pump 15 comprise stainless steel or other bacteria and fungus resistant materials. Pump 15 may be any suitable pump, for example, a Roper Type 1 gear pump, Roper Pump Company (Commerce Georgia) or a Dayton Pressure Booster Pump Model 2P372E, Dayton Electric Co. (Niles, Ill.). Pump 15 is fluid communication with HSD 30.

Gas stream 20 is injected, bubbled, diffused, or introduced into media stream 12. Gas stream 20 is directed to HSD 30. Gas stream 20 comprises air. Gas stream 20 comprises a carbon-containing gas or gas stream. Gas stream 20 further comprises carbon dioxide ($CO_2$) stream 22 and nitrogen stream 24. $CO_2$ stream 22 comprises gaseous $CO_2$, for example pressurized $CO_2$. Further, $CO_2$ stream 22 comprises air, for example air from a $CO_2$ rich environment such as a parking garage, an airport, a building, or air brought in from a city or urban environment. Without limitation by theory, the implementation of air from a $CO_2$ rich environment comprises sequestering the $CO_2$, recycling the $CO_2$, or reducing the $CO_2$ contribution to atmospheric pollutants. Nitrogen stream 24 comprises nitrogen-containing gases, for example gaseous nitrogen ($N_2$) and other nitrogen compounds. Nitrogen stream 24 comprises nitrogen ($N_2$), oxides of nitrogen, ammonia, nitrates, and other nitrogen containing compounds, without limitation. $CO_2$ stream 22 and nitrogen stream 24 are introduced to gas stream 20 in a controlled ratio. The ratio of $CO_2$ stream 22 to nitrogen stream 24 is regulated to maximize algal growth.

Media stream 12 and gas stream 20 are introduced to HSD 30. Media stream 12 and gas stream are injected into HSD 30 via pump 15. In certain instances, pump 15 injects media stream 12 and gas stream 20 is introduced separately. Media stream 12 and gas stream 20 are introduced to HSD 30 for processing. As discussed in detail above, HSD 30 is a mechanical device that utilizes, for example, a stator rotor mixing head with a fixed gap between the stator and rotor. In HSD, gas stream 20 and media stream 12 are mixed to form an emulsion comprising microbubbles and nanobubbles of nitrogen and $CO_2$ containing gas from gas stream 20. The resultant dispersion comprises an average bubble size less than about 1.5 µm; alternatively, the mean bubble size is less than from about 0.1 µm to about 1.5 µm. The resultant dispersion comprises bubbles with a submicron mean bubble diameter. The mean bubble size is less than about 400 nm; more preferably, less than about 100 nm. The high shear mixing produces gas bubbles capable of remaining dispersed at atmospheric pressure for about 15 minutes or longer depending on the bubble size. The emulsion may further comprise a micro-foam or a nanofoam. In certain configurations, APS 100 comprises a plurality of HSD 30 operated in series.

Not to be limited by a specific method, it is known in emulsion chemistry that submicron particles dispersed in a liquid undergo movement primarily through Brownian motion effects. Thus, submicron gas particles created by the HSD 30 have greater mobility through boundary layers of suspended solids in media stream 12 thereby facilitating and accelerating algal uptake, growth, and APS 100 efficiency.

HSD 30 produces an emulsion stream 32. Emulsion stream 32 is directed to bioreactor 35. Bioreactor 35 comprises an open pond, a translucent tank, translucent tube, deep tank, lighted tank, flowing reactor, or other arrangement without limitation. Bioreactor 35 comprises any bioreactor having a means to grow algae known to one skilled in the art. Bioreactor 35 comprises a plurality of monitors and automated circuits to maintain preferred conditions. Bioreactor 35 comprises a heater or other thermal elements configured to heat or warm the contents and maintain a preferred temperature. Bioreactor 35 comprises light conduits, for instance fiber-optic cables to transmit light into the maximal volume of bioreactor. Bioreactor 35 comprises an agitating means, such as a stirrer to expose algae to additional light irradiation. Without limitation by theory, algal growth rates are effected by exposure to light, a mechanical agitating means is configured to expose the algae to light or light source irradiation.

In certain instance bioreactor 35 comprises a light source 34 configured for delivering light to the bioreactor 30. Further, light source 34 comprises the sun. Light source 34 is configured to supplement solar light spectrum in certain ranges. Light source 34 comprises an artificial natural light, i.e. a light that transmits in a similar spectrum and intensity as solar light. Alternatively, light source 34 comprises a light configured to irradiate the bioreactor with a preferred spectrum of light. Light source 34 is configured to heat or warm bioreactor 35 to a temperature favorable for algal growth.

Algae stream 33 is introduced to bioreactor 35. Algae stream 33 comprises an inoculation stream. Algae stream 33 comprises algae in an inoculation media. Algae stream 33 may comprise an inoculation tank, for growing a volume of algae for inoculating the bioreactor 35. Algae stream 33 comprises a concentrated stream or slurry of algae for inoculating emulsion stream 32. Algae stream 33 comprises a stream or slurry of algae for growth in the bioreactor 35. In certain instances, the bioreactor 35 is prefilled with emulsion stream 32; alternatively, algae stream 33 and emulsion stream 32 are introduced into bioreactor 35 simultaneously. Algae stream 33 and emulsion stream 32 are allowed to circulate through bioreactor 35.

Without limitation by theory, algae in bioreactor 35 grow, divide and multiply by consumption of biomolecules in media stream 12 and gas stream 20. The consumed portions of the media stream 12 and gas stream 20 are reintroduced to the bioreactor 35 by emulsion stream 32. In certain instances, the reintroduction of biomolecules comprises make-up streams. The make-up streams follow the original process stream described herein. Further, the make-up stream may comprise an alternative composition as preferred to maintain conditions in the bioreactor 35. Bioreactor 35 comprises monitors for tracking composition of emulsion stream 32 make-up streams and adjusting the composition of media stream 12 and gas stream 20.

Bioreactor 35 is drained by algae outlet 37 to a filter 40. Bioreactor 35 may be continuously drained, such that a constant flow of algae is removed from bioreactor 35. Alternatively, bioreactor 35 is drained on a batch-process basis. Algae withdrawn by algae outlet 37 are separated from the media by filter 40. Filter 40 comprises a screen filter, a centrifuge, a skimmer, a dryer, a vacuum, or another method known to remove aqueous media from algae. Filter 40 forms waste liquid stream 42 and algae slurry 43.

Waste liquid stream 42 is further separated to form liquid recycle stream 46 and biowaste stream 45 by a separator 44. Liquid recycle stream 46 comprises aqueous media and dissolved compounds. Liquid recycle stream 46 is returned to the media stream 12. In certain instances, liquid recycle stream 46 comprises make-up liquid or make-up nutrients. Biowaste stream 45 comprises suspended solids, algal remains, dead algae, and other solid wastes. Biowaste stream 45 is directed to a biomaterial (BM) processor 56. BM processor 56 comprises a digester, a fermenter, a pulper, or a cooker, without limitation for processing the biowaste stream 45. BM processor 56 may comprise a burner for burning biowaste stream 45 for energy, for example to maintain bioreactor 35 temperature.

Algae slurry 43 is directed to a lysis reactor 50. In certain instances, the lysis reactor 50 comprises a dewatering step or dryer to remove remaining water from algae slurry 43. Lysis reactor 50 comprises a means to lyse or rupture the algae in algae slurry 43. Lysis reactor 50 comprises buffer stream 53. Buffer stream 53 comprises buffers, chelators, anti-oxidants, and other compounds understood in the art to resist degradation of lipids and hydrocarbons. Lysis reactor 50 is further configured to separate the lipids and hydrocarbons from other cellular molecules. Lysis reactor 50 may comprise a separator for an algal hydrocarbon stream 52 and an algal waste stream 54. Lysis reactor 50 forms an algal hydrocarbon stream 52 and an algal waste stream 54.

Algal waste stream 54 is directed to biomaterial (BM) processor 56. Algal waste stream 54 comprises cellular components, proteins, molecules, membranes, and the like without limitation. Algal waste stream 54 carries cellular components that are not suitable for refining into a BM processor 56 comprising a digester, a fermenter, a pulper, or a cooker, without limitation, for processing biowaste stream 45. BM processor 56 may comprise a burner for burning biowaste stream 45 for energy, for example to maintain the temperature of bioreactor 35.

Algal hydrocarbon stream 52 is directed to a cracking process in a hydrocarbon reactor 60 to produce a raw hydrocarbon stream 62. Raw hydrocarbon stream 62 comprises paraffins, alkanes and other saturated hydrocarbons Alternatively, raw hydrocarbon stream 62 comprises alkenes, olefins, alkynes, and other unsaturated hydrocarbons, without limitation. In certain instances, raw hydrocarbon stream 62 comprises, without limitation, carboxylic acids, lactic acids, and other organic acids. Raw hydrocarbon stream 62 further comprises lipids, fatty acids, and polysaccharides.

Raw hydrocarbon stream 62 is directed to refinery 64 for the production of a liquid hydrocarbon product 66. Refinery 64 comprises hydrocracking, filtering, separating, reacting, distilling, and other process known in the arts for the production of a liquid hydrocarbon product 66. Liquid hydrocarbon product 66 comprises naphtha, kerosene, gasoline, diesel, and combinations thereof.

Figure 3:
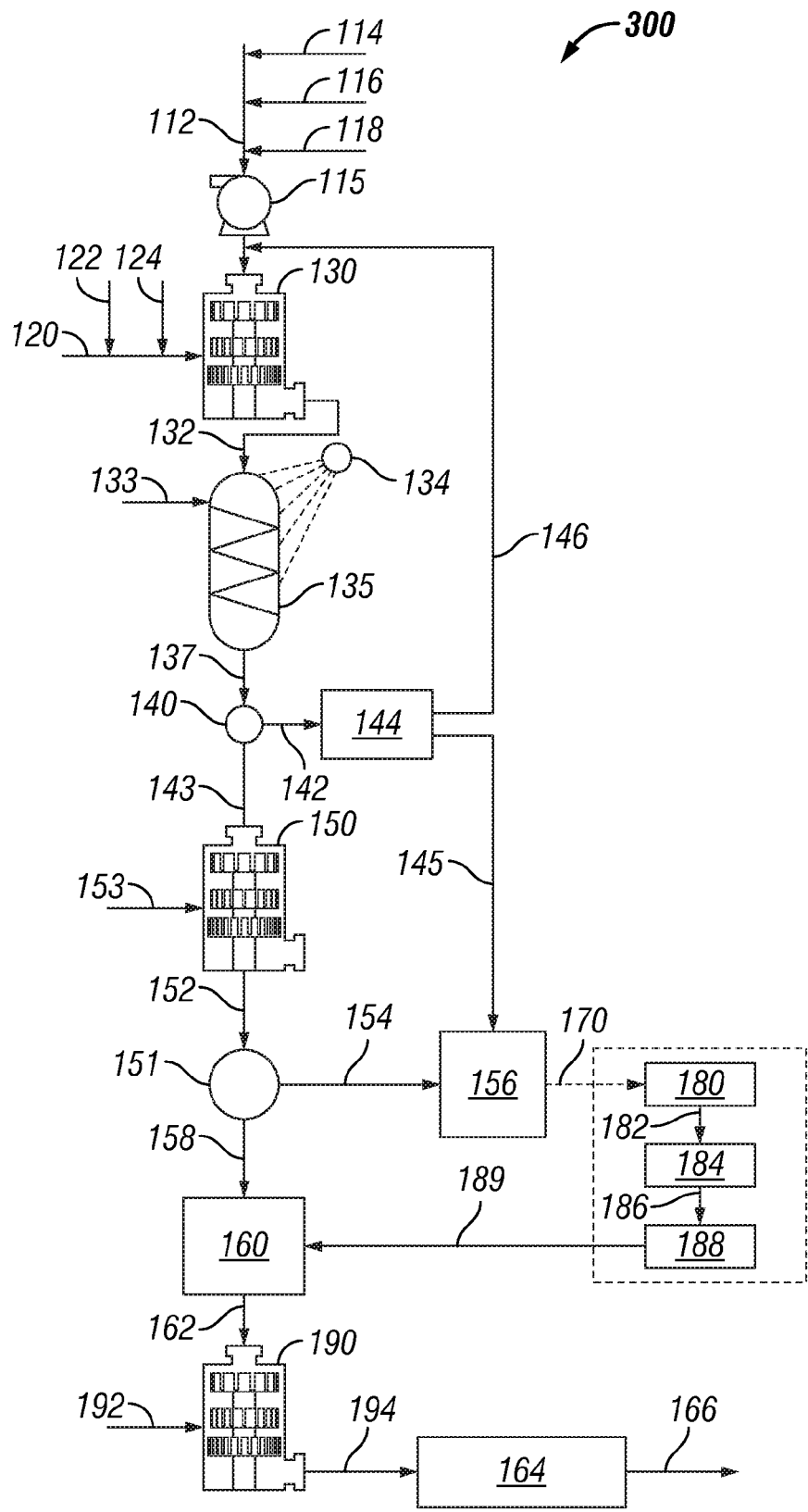
FIG. 3 is a process flow diagram according to an alternate embodiment of the present disclosure for high shear algae processing.

Multiple High Shear Processes and System for Algae Growth and Processing: Referring to FIG. 3, illustrating a multi-shear algae processing system (MAPS) 300. MAPS 300 comprises high shear device (HSD) 130, bioreactor 135, high shear lysis device 150 and hydrocarbon reactor 160. MAPS 300 is configured to optimize the growth and harvesting of algae. MAPS 300 is configured for introducing a media stream, comprising nutrients, and gases to HSD 130 prior to inoculation with a selected algal species and introduction to a bioreactor 135. Further, MAPS 300 is configured to isolate lipids, oils, and polysaccharides, herein hydrocarbons, from algae. MAPS 300 is configurable to comprise a plurality of HSD 130 or similar devices. In certain applications, MAPS 300 may be configured for the homogenization of the hydrocarbons.

Algae are grown and/or cultured in a broth or substrate, such as media stream 112. In certain instances, the media stream 112 comprises sugars, proteins, amino acids, and other biomacromolecules suitable to replicate and/or simulate the growth environment of the algae. The presence of these biomolecules in media stream 112 comprises additional molecules for the algal life cycle. Further, the media stream 112 comprises salinity similar to the natural environment of the algae. For instance, the media stream 112 comprises a salinity to replicate an aquatic, a marine, or a brackish environment. Generally, water; preferably distilled water, is used to culture the algae. The water is sterile and free from all contaminants. Any appropriate culture mediums known to those of skill in the art may be used as media stream 112 depending on the specific algae species.

In certain instances, media stream 112 is supplemented to improve growth of algae. Media stream 112 comprises a pH enhancer stream 114, an electrolyte stream 116, and a nutrient stream 118. In instances, pH enhancer stream 114, electrolyte stream 116, and nutrient stream 118 comprise media stream 112. Alternatively, pH enhancer stream 114, electrolyte stream 116, and nutrient stream 118 are mixed with media stream 112 to alter, regulate the composition of media stream 112. Further, pH enhancer stream 114, electrolyte stream 116, and nutrient stream 118 are introduced to media stream 112 as a make up stream for replacing the media and nutrients consumed by the algal culture.

A pH enhancer stream 114 is mixed with media stream 112. A pH enhancer stream 114 comprises any chemical understood by one skilled in the art to alter pH. Alternatively, a pH enhancer stream comprises any chemical understood by one skilled in the art to resist pH changes, for instance a buffer. The pH enhancer stream 114 comprises a salt, a buffer, an anion, or a cation without limitation. In instances, pH enhancer stream 114 is introduced directly to media stream 112; alternatively, pH enhancer stream 114 is introduced to MAPS 300 in any point in the process.

Media stream 112 is supplemented by an electrolyte stream 116. Without limitation by theory, an electrolyte comprises any chemical having free ions. Alternatively, an electrolyte comprises an electrically conductive medium, such as an ionic solution. In certain instances, electrolyte stream 116 comprises magnesium, calcium, sodium, potassium, chloride, phosphate, or carbonate ions, without limitation. Electrolyte stream 116 comprises compounds conducive for the synthesis of chlorophyll; alternatively, for the synthesis of algal hydrocarbons.

Media stream 112 is supplemented with a nutrient stream 118. In certain instances, nutrient stream 118 introduces nutrients, such as, but not limited to, sugars, lipids, and biomacromolecules. Alternatively, nutrient stream 118 comprises a make-up stream, configured to reintroduce nutrients to media stream 112. Nutrient stream 118 may further comprise antibiotics or antifungal compounds for controlling contaminants in media stream 112.

Media stream 112 is directed to pump 115. Pump 115 is used to provide a controlled flow to HSD 130 and MAPS 300. Pump 115 increases the pressure of the media stream 112 to greater than about 203 kPa (2 atm). Alternatively, the pump 115 may pressurize media stream 112 to a pressure of greater than about 2030 kPa (20 atm). The increased pressure of media stream 112 can be used to accelerate reactions and diffusion of molecules. In further instances, the increased pressure of media stream 112 ensures sterility of the media stream. Without limitation by theory, sterilizing media stream 112 eliminates competitors for nutrients in media stream 112. The limiting factor for pressure in MPS 300 may be the pressure limitations of pump 115 and HSD 130. Preferably, all contact parts of pump 115 comprise stainless steel or other bacteria and fungus resistant materials. Pump 115 may be any suitable pump, for example, a Roper Type 1 gear pump, Roper Pump Company (Commerce Georgia) or a Dayton Pressure Booster Pump Model 2P372E, Dayton Electric Co. (Niles, Ill.). Pump 115 is fluid communication with HSD 130.

Gas stream 120 is injected, bubbled, diffused, or introduced into media stream 112. Gas stream 120 is directed to HSD 130. Gas stream 120 comprises air. Gas stream 120 further comprises carbon dioxide ($CO_2$) stream 122 and nitrogen stream 124. $CO_2$ stream 122 comprises gaseous $CO_2$, for example pressurized $CO_2$. Further, $CO_2$ stream 22 comprises air, for example air from a $CO_2$ rich environment such as a parking garage, an airport, a building, or air brought in from a city or urban environment. Without limitation by theory, the implementation of air from a $CO_2$ rich environment comprises sequestering the $CO_2$, recycling the $CO_2$, or reducing the $CO_2$ contribution to atmospheric pollutants. Nitrogen stream 124 comprises gaseous nitrogen ($N_2$) and other nitrogen compounds. Nitrogen stream 124 comprises nitrogen ($N_2$), oxides of nitrogen, ammonia, nitrates, and other nitrogen containing compounds, without limitation. $CO_2$ stream 122 and nitrogen stream 124 are introduced to gas stream 120 in a controlled ratio. The ratio of $CO_2$ stream 122 to nitrogen stream 124 is regulated to maximize algal growth.

Media stream 112 and gas stream 120 are introduced to HSD 130. Media stream 112 and gas stream 120 are injected into HSD 130 via pump 115. In certain instances, pump 115 injects media stream 112 and gas stream 120 is introduced separately. Media stream 112 and gas stream 120 are introduced to HSD 30 for processing. As discussed in detail above, HSD 130 is a mechanical device that utilizes, for example, a stator rotor mixing head with a fixed gap between the stator and rotor. In HSD, gas stream 120 and media stream 112 are mixed to form an emulsion comprising microbubbles and nanobubbles of nitrogen and $CO_2$ containing gas from gas stream 120. The resultant dispersion comprises an average bubble size less than about 1.5 μm; alternatively, the mean bubble size is less than from about 0.1 μm to about 1.5 μm.

The resultant dispersion comprises bubbles with a submicron mean bubble diameter. The mean bubble size is less than about 400 nm; more preferably, less than about 100 nm. The high shear mixing produces gas bubbles capable of remaining dispersed at atmospheric pressure for about 15 minutes or longer depending on the bubble size. The emulsion may further comprise a micro-foam or a nanofoam. In certain configurations, MAPS 300 comprises a plurality of HSD 130 operated in series for forming a nanofoam of gas stream 120 in the media stream 112.

Not to be limited by a specific method, it is known in emulsion chemistry that submicron particles dispersed in a liquid undergo movement primarily through Brownian motion effects. Thus, submicron gas particles created by the HSD 130 have greater mobility through boundary layers of suspended solids in media stream 112 thereby facilitating and accelerating algal uptake, growth, and MAPS 300 efficiency.

HSD 130 produces an emulsion stream 132. Emulsion stream 132 is directed to bioreactor 135. Bioreactor 135 comprises an open pond, a translucent tank, translucent tube, deep tank, lighted tank, flowing reactor, or other arrangement without limitation. Bioreactor 135 comprises any bioreactor having a means to grow algae known to one skilled in the art. Bioreactor 135 comprises a plurality of monitors and automated circuits to maintain preferred conditions. Bioreactor 135 comprises a heater or other thermal element configured to heat or warm the contents and maintain a preferred temperature. Bioreactor 135 comprises light conduits, for instance fiber-optic cables to transmit light into the maximal volume of bioreactor. Bioreactor 135 comprises an agitating means, such as a stirrer to expose algae to additional light irradiation. Without limitation by theory, algal growth rates are effected by exposure to light, a mechanical agitating means is configured to expose the algae to light or light source irradiation.

In certain instance bioreactor 135 comprises a light source 134 configured for delivering light to the bioreactor 130. Further, light source 134 comprises the sun. Light source 134 is configured to supplement solar light spectrum in certain ranges. Light source 134 comprises an artificial natural light, i.e. a light that transmits in a similar spectrum and intensity as solar light. Alternatively, light source 134 comprises a light configured to irradiate the bioreactor with a preferred spectrum of light. Light source 134 is configured to heat or warm bioreactor 135 to a temperature favorable for algal growth.

Algae stream 133 is introduced to bioreactor 135. Algae stream 133 comprises an inoculation stream. Algae stream 133 comprises algae in an inoculation media. Algae stream 133 may comprise an inoculation tank, for growing a volume of algae for inoculating the bioreactor 135. Algae stream 133 comprises a concentrated stream or slurry of algae for inoculating emulsion stream 132. Algae stream 133 comprises a stream or slurry of algae for growth in the bioreactor 135. In certain instances, the bioreactor 135 is prefilled with emulsion stream 132; alternatively, algae stream 133 and emulsion stream 132 are introduced into bioreactor 135 simultaneously. Algae stream 133 and emulsion stream 132 are allowed to circulate through bioreactor 135.

Without limitation by theory, algae in bioreactor 135 grow, divide and multiply by consumption of biomolecules in media stream 112 and gas stream 120. The consumed portions of the media stream 112 and gas stream 120 are reintroduced to the bioreactor 135 by emulsion stream 132. In certain instances, the reintroduction of biomolecules comprises make-up streams. The make-up streams follow the original process stream described herein. Further, the make-up stream may comprise an alternative composition as preferred to maintain conditions in the bioreactor 135. Bioreactor 135 comprises monitors for tracking composition of emulsion stream 132 make-up streams and adjusting the composition of media stream 112 and gas stream 120.

Bioreactor 135 is drained by algae outlet 137 to a filter 140. Bioreactor 135 may be continuously drained, such that a constant flow of algae is removed from bioreactor 135. Alternatively, bioreactor 135 is drained on a batch-process basis. Algae withdrawn by algae outlet 137 are separated from the media by filter 140. Filter 140 comprises a screen filter, a centrifuge, a skimmer, a dryer, a vacuum, or another method known to remove aqueous media from algae. Filter 140 forms waste liquid stream 142 and algae slurry 143.

Waste liquid stream 142 is further separated to form liquid recycle stream 146 and biowaste stream 145 by a separator 144. Liquid recycle stream 146 comprises aqueous media and dissolved compounds. Liquid recycle stream 146 is returned to the media stream 112. In certain instances, liquid recycle stream 146 comprises make-up liquid or make-up nutrients.

Biowaste stream 145 comprises suspended solids, algal remains, dead algae, and other solid wastes. Biowaste stream 145 is directed to a biomaterial (BM) processor 156. BM processor 156 comprises, without limitation, a digester, a fermenter, a pulper, or a cooker for processing biowaste stream 145. BM processor 156 may comprise a burner for burning biowaste stream 145 for energy, for example to maintain the temperature of bioreactor 135.

Algae slurry 143 is directed to a lysis high shear device, or a second high shear device (HSD) 150. In certain instances, the HSD 150 comprises a dewatering step or dryer to further remove water from algae slurry 143. HSD 150 comprises a means to lyse or rupture the algae in algae slurry 143. Lysis reactor 150 comprises buffer stream 153. Buffer stream 153 comprises buffers, chelators, anti-oxidants, and other compounds understood in the art to resist degradation of lipids and hydrocarbons. Without limitation by theory, HSD 150 or lysis high shear device is configured to mechanically shear the algae in buffer. HSD 150 forms globules of algal biomolecules in buffer. In certain instances, the HSD 150 forms cellular emulsion stream 152 comprising an emulsion of algal components, comprising hydrocarbons, in the buffer. In instances, algal components comprise algal hydrocarbons and algal biomolecules. Algal biomolecules comprise all extra- and intracellular molecules, proteins, enzymes, and materials from a lysed algal cell that are not suitable for refining. HSD 150 is configured to form cellular emulsion stream 152 by operating as described hereinabove.

Cellular emulsion stream 152 is processed by a separator 151 to separate the lipids and hydrocarbons from other cellular molecules. Cellular emulsion stream 152 may be directed to separator 151 to form an algal hydrocarbon stream 158 and an algal waste stream 154. Algal hydrocarbon stream 158 is directed to a hydrocarbon processor, or cracker 160.

Algal waste stream 154 is directed to biomaterial (BM) processor 156. Algal waste stream 154 comprises algal biomolecules. Further, algal waste stream comprises 154 comprises cellular components, proteins, molecules, membranes, and the like without limitation. Algal waste stream 154 comprising cellular components that are not suitable for refining is directed into a BM processor 156 comprising, without limitation, a digester, a fermenter, a pulper, or a cooker for processing biowaste stream 154. BM processor 156 may comprise a burner for burning biowaste stream 145 for energy, for example to maintain the temperature of bioreactor 135. In certain instances, BM processor 156 produces a biomass stream 170 for feeding to a fermenter 180. The fermenter products 182 are processed through a dewatering and thermal conversion 184 to produce an alcohol stream 186.

Alcohol stream 186 is processed through additional steps, for instance hydrogenation 188, to form a supplemental hydrocarbon stream 189. Supplemental hydrocarbon stream 189 is directed to hydrocarbon processor, or cracker 160.

Cracker 160 comprises any process known to one skilled in the arts to produce a raw hydrocarbon stream 162. Raw hydrocarbon stream 162 comprises paraffins, alkanes and other saturated hydrocarbons. Alternatively, raw hydrocarbon stream 162 comprises alkenes, olefins, alkynes, and other unsaturated hydrocarbons, without limitation. In certain instances, the raw hydrocarbon stream 162 comprises carboxylic acids, lactic acids, and other organic acids without limitation. Raw hydrocarbon stream 162 further comprises lipids, fatty acids, and polysaccharides.

In certain instances, raw hydrocarbon stream 162 is directed to a homogenizing high shear device (HSD) 190. Homogenizing HSD 190 comprises a reactant stream 192. Reactant stream 192 comprises a gaseous reactant, a liquid reactant, a catalyst, or another reactant, without limitation. Homogenizing HSD 190 is configured to form an emulsion as described hereinabove, comprising the reactant stream 192 in the raw hydrocarbon stream 162. Homogenizing HSD 190 forms a hydrocarbon precursor emulsion 194.

Hydrocarbon precursor emulsion 194 is directed to refinery 164 for the production of a liquid hydrocarbon product 166. Refinery 164 comprises hydrocracking, filtering, separating, reacting, distilling, and any other process known in the arts for the production of a liquid hydrocarbon product 166. Liquid hydrocarbon product 166 comprises naphtha, kerosene, gasoline, diesel, and combinations thereof.

Accordingly, the scope of protection is not limited by the description set out above but is only limited by the claims that follow, that scope including all equivalents of the subject matter of the claims. The claims are incorporated into the specification as an embodiment of the present invention. Thus, the claims are a further description and are an addition to the preferred embodiments of the present invention. The discussion of a reference herein is not an admission that it is prior art to the present invention, especially any reference that may have a publication date after the priority date of this application. The disclosures of all patents, patent applications, and publications cited herein are hereby incorporated by reference, to the extent they provide exemplary, procedural, or other details supplementary to those set forth herein.

We claim:

1. A method for alga-culture, the method comprising:
   forming a mixture of a gaseous stream and a media steam comprising nutrients for algae growth;
   forming an emulsion by introducing the mixture into a high shear device and therein subjecting the mixture to a shear rate of at least 20,000 s$^{-1}$, wherein the emulsion comprises gas bubbles with a mean diameter of less than about 5 µm, and wherein the high shear device comprises at least one toothed rotor and at least one stator;
   introducing the emulsion into a bioreactor; and
   introducing an algae into the bioreactor for culturing the algae culture.

2. The method of claim 1 wherein the gaseous stream comprises gases chosen from carbon dioxide, nitrogen, oxygen, atmospheric gases, and combinations thereof.

3. The method of claim 1 further comprising pumping a reactant stream comprising the media stream to a pressure of at least about 203 kPa to produce a pressurized stream.

4. The method of claim 1 wherein the gas bubbles in the emulsion have an average diameter of less than about 1.5 µm.

5. The method of claim 1 wherein forming the emulsion comprises rotating the at least one toothed rotor at a tip speed of at least about 20 m/s.

6. The method of claim 4 wherein forming the emulsion comprises producing a localized pressure of about 1000 MPa at the tip of the at least one toothed rotor.

7. The method of claim 1 wherein forming the emulsion comprises an energy expenditure of at least 1000 W/m$^3$.

8. A method for culturing algae for producing liquid hydrocarbons, the method comprising:
   forming a mixture of a gaseous stream and a media stream comprising nutrients for algae growth;
   forming a first emulsion by introducing the mixture into a high shear device and therein subjecting the mixture to shear, wherein the first emulsion comprises gas bubbles with a mean diameter of less than about 5 µm, and wherein the high shear device comprises at least one rotor and at least one stator;
   introducing the first emulsion into a bioreactor;
   introducing at least one algae into the first emulsion in the bioreactor, for producing an algae culture;
   forming a second emulsion comprising a portion of the algae culture and a buffer utilizing a high shear device, wherein the second emulsion comprises lysed algal-component globules with a mean diameter of less than about 5 µm, and wherein the lysed algal component globules comprise algal hydrocarbons and algal biomolecules;
   separating algal hydrocarbons from algal biomolecules in the second emulsion; and
   processing the algal hydrocarbons to produce liquid hydrocarbons.

9. The method of claim 8, wherein the gaseous stream comprises at least one gas chosen from the group consisting of carbon dioxide, nitrogen, oxygen, atmospheric gases, and combinations thereof.

10. The method of claim 8, wherein forming a first emulsion comprises pumping the media stream to a pressure of at least about 203 kPa to produce a pressurized stream.

11. The method of claim 10, wherein pumping the media stream further comprises sterilizing the media stream.

12. The method of claim 8, wherein forming a second emulsion further comprises dewatering the algae culture to form an algae slurry.

13. The method of claim 8, wherein separating the algal hydrocarbons from algal biomolecules comprises processing the algal biomolecules to form liquid hydrocarbons.

14. The method of claim 13, wherein processing the algal biomolecules comprises:
   fermenting the algal biomolecules to form alcohols; and
   reacting the alcohols to form liquid hydrocarbons.

15. The method of claim of claim 8, wherein processing the liquid hydrocarbons further comprises forming a third emulsion comprising a catalyst and the liquid hydrocarbons in a high shear device; wherein the third emulsion comprises catalyst globules with a mean diameter of less than about 5 µm.

16. The method of claim 8 wherein forming the first emulsion, the second emulsion, or both comprises rotating at least one rotor at a tip speed of at least about 20 m/s.

17. The method of claim 8 wherein forming the emulsion, the second emulsion, or both comprises producing a localized pressure of about 1000 MPa at the tip of at least one rotor.

18. The method of claim 8 wherein forming the first emulsion comprises subjecting the gaseous stream and the media to a shear rate of at least about 20,000 s$^{-1}$.

19. The method of claim 8 wherein forming the first emulsion, the second emulsion, or both comprises an energy expenditure of at least 1000 W/m$^3$.

\* \* \* \* \*